US007405214B2

(12) United States Patent
Lee et al.

(10) Patent No.: US 7,405,214 B2
(45) Date of Patent: Jul. 29, 2008

(54) NUCLEOSIDE DERIVATIVES AND THERAPEUTIC USE THEREOF

(75) Inventors: Young Bok Lee, Rockville, MD (US); Chang Ho Ahn, Potomac, MD (US); Won Jun Choi, Frederick, MD (US); Lak Shin Jeong, Seoul (KR); Sang Kook Lee, Seoul (KR)

(73) Assignee: Rexahn Corporation, Rockville, MD (US)

( * ) Notice: Subject to any disclaimer, the term of this patent is extended or adjusted under 35 U.S.C. 154(b) by 145 days.

(21) Appl. No.: 11/095,686

(22) Filed: Apr. 1, 2005

(65) Prior Publication Data

US 2005/0222185 A1 Oct. 6, 2005

Related U.S. Application Data

(60) Provisional application No. 60/558,141, filed on Apr. 1, 2004.

(51) Int. Cl.
*A01N 43/04* (2006.01)
*A01N 43/54* (2006.01)
*A61K 31/70* (2006.01)
*A61K 31/505* (2006.01)
*C07D 239/00* (2006.01)

(52) U.S. Cl. ............... 514/247; 514/42; 514/49; 514/50; 514/256; 514/269; 536/18.7; 536/22.1; 536/28.1; 544/242

(58) Field of Classification Search ............. 514/23, 514/42, 49, 50, 247, 256, 269; 536/1.11, 536/18.7, 22.1, 28.1; 544/242
See application file for complete search history.

(56) References Cited

U.S. PATENT DOCUMENTS 4,975,434 A * 12/1990 Marquez et al. ............ 514/274
6,949,563 B2 * 9/2005 Wynne et al. ............... 514/300

FOREIGN PATENT DOCUMENTS

WO   WO-02/32920 A2   4/2002

OTHER PUBLICATIONS

Marquez et al., J Med. Chem., 1988, 31, 1687-94.*
Jeong et al., J Med Chem, 2003, 46(2), 201-203.*
Marquez et al., J. Med Chem, 1988, vol. 31, pp. 1687-1694.*

Choi et al., "Preparative and Stereoelective Synthesis of the Versatile Intermediate for Carbocyclic Nucleosides: Effects of the Bulky Protecting Groups to Enforce Facial Selectivity", J. Org. Chem. 2004, 69, 2634-2636.
Chu C K et al: "Antiviral Activity of Cyclopentenyl Nucleosides Against Orthopox Viruses (Smallpox, Monkeypox and Cowpox)." Bioorganic & Medicinal Chemistry Letters, Jan. 6, 2003, vol. 13, No. 1, pp. 9-12.
Hronowski et al: "Synthesis of cyclopentane analogs of 5-fluorouracil nucleosides" Canadian Journal of Chemistry, National Research Council. Ottawa, CA, vol. 70, No. 4, 1992, pp. 1162-1169.
Jeong Lak Shin et al: "Design, Synthesis, and Biological Evaluation of Fluoroneplanocin A as the Novel Mechanism-Based Inhibitor of S-Adenosylhomocysteine Hydrolase." Journal of Medicinal Chemistry. Jan. 16, 2003, vol. 46, No. 2, pp. 201-203.

* cited by examiner

*Primary Examiner*—Shaojia Anna Jiang
*Assistant Examiner*—Traviss C. McIntosh, III
(74) *Attorney, Agent, or Firm*—Venable LLP; Michael A. Gollin; Keith G. Haddaway

(57) ABSTRACT

The present invention relates to nucleoside derivatives represented by general formulas I and II, their synthetic methods and their pharmacologically acceptable salts thereof, and compositions containing such compounds. Methods for treating hyperproliferative disorders by administering the compounds are also included.

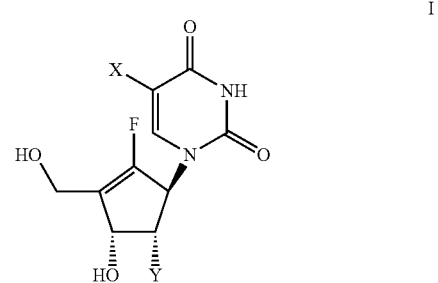

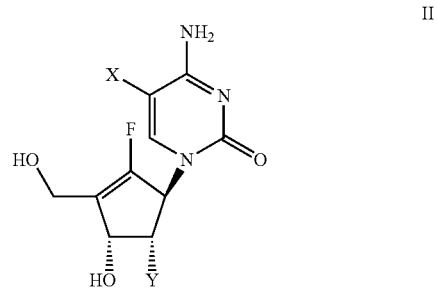

18 Claims, 1 Drawing Sheet

Fig. 1. RX-3117 causes the inhibition of tumor growth in nude mice sc-injected with HCT116 human colon carcinoma cells.

NUCLEOSIDE DERIVATIVES AND THERAPEUTIC USE THEREOF

This application claims priority of U.S. Provisional Application No. 60/558,141 filed Apr. 1, 2004, which is incorporated herein by reference in its entirety.

FIELD OF THE INVENTION

This application relates to nucleoside compounds, and related synthetic methods, compositions and their therapeutic methods for the treatment of hyperproliferative disorders, including cancers, by administering nucleoside compounds.

BACKGROUND OF THE INVENTION

There is a need for novel nucleoside compounds as therapeutic molecules for the treatment of disorders such as cancers. Methods of using both known and novel nucleoside compounds for the treatment of particular disorders are needed.

SUMMARY OF THE INVENTION

Figure 1:
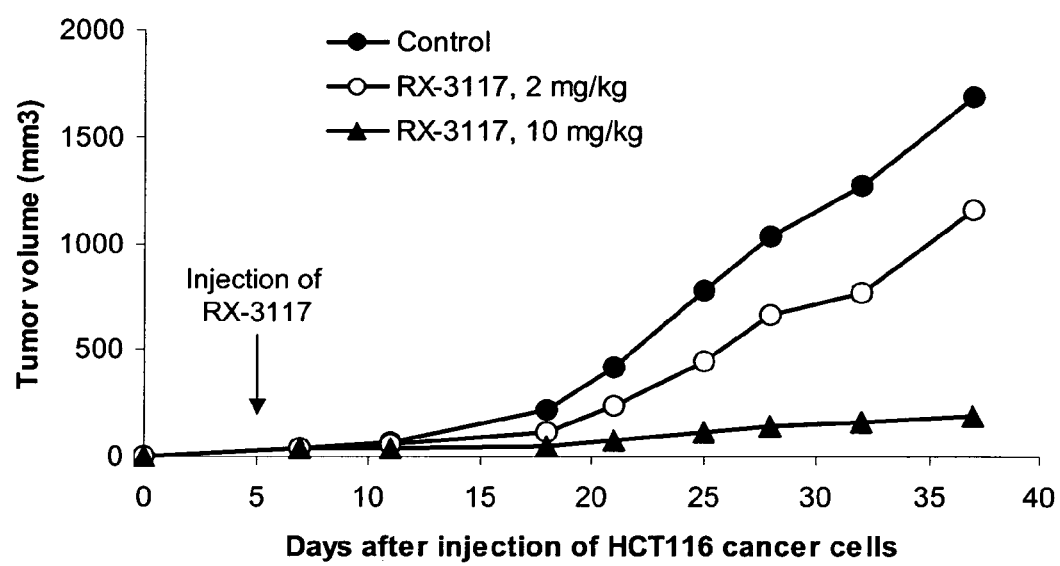
FIG. 1 is a graph showing the inhibition of tumor growth by RX-3117 in nude mice subcutaneously injected with HCT116 human colon carcinoma cells.

A series of nucleoside compounds were synthesized and analyzed for therapeutic activities, including anti-cancer activities. Nucleoside compounds of the invention are demonstrated as useful for the treatment of hyperproliferative disorders, including tumors, such as breast tumors, colon tumors, lung tumors and stomach tumors.

DETAILED DESCRIPTION OF THE INVENTION

Definitions

The terms "nucleoside", "nucleoside compound", and "nucleoside derivative" are used interchangeably in this application to mean compounds of formula I or II, as defined below. All scientific and technical terms used in this application have meanings commonly used in the art unless otherwise specified. As used in this application, the following words or phrases have the meanings specified.

As used herein, "pharmaceutically acceptable carrier" means any material which, when combined with a compound of the invention, allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, in the present invention, the nucleoside derivative can be bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

"Treating" means to inhibit, reduce, modulate, ameliorate, or block at least one symptom that characterizes a pathologic condition, in a subject threatened by, or afflicted with, the condition.

A "hyperproliferative disorder" is a disorder characterized by abnormal proliferation of cells, and generically includes skin disorders such as psoriasis as well as benign and malignant tumors of all organ systems. This latter class of hyperproliferative disorders includes, for instance, breast carcinomas (including lobular and duct carcinomas) and other solid tumors, carcinomas, sarcomas, and cancers including carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage.

The present invention comprises nucleoside compounds and their use in the treatment of a hyperproliferative disorder, disease or condition in a subject (e.g., a human patient or other animal subject). Methods according to the invention comprise administering to a subject an effective amount of a nucleoside compound according to the invention. Such a treatment can, e.g., prevent, ameliorate, and/or inhibit symptoms of the hyperproliferative condition, and/or can prevent or inhibit cellular proliferation or growth, for instance in a tumor, such as a malignant neoplasm. A treatment strategy of the invention would decrease the tumor burden, at least to a measurable degree, and improve survival of patients suffering from the hyperproliferative condition. Among the diseases, disorders and conditions susceptible to treatment by agents of the invention are neoplasms, and more specifically tumors of various origins (lung, colon, stomach, smooth muscle, esophagus, non-Hodgkin's lymphoma, non-small cell lung cancer, etc.).

Compounds Useful in Methods According to the Invention

Compounds useful in methods of the invention include nucleosides having the formula I:

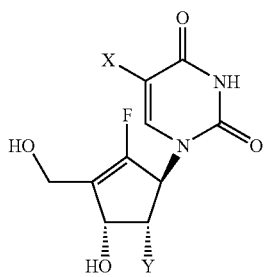

wherein Y=H or OH and X=H, F, Cl, Br, I, or $CH_3$.

Also included are compounds having formula II:

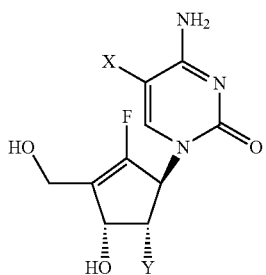

wherein Y=H or OH and X=H, F, Cl, Br, or I. Although illustrated in the sterochemical conformations based on naturally occurring sugars, the invention includes related steroisomers, and mixtures. Related steroisomers include enantiomers, diastereomers and mixtures thereof, and reacemic mixtures and mixtures of two or more diastereomers. The invention also includes pharmaceutically acceptable salts of these compounds.

Compounds of the invention can be very active against a wide range of hyperproliferatvie diseases, including tumors. For example, compounds according to the invention can be active against tumors of the ovary, tumors of the breast, cervical tumors, tumors of the prostate, tumors of the liver, lung tumors, kidney tumors, colon tumors, pancreatic tumors, brain tumors, stomach tumors and melanoma. By very active, it is meant that a compound can have an $IC_{50}$ of 5.0 μM or less, 2.0 μM or less, 1.0 μM or less, or 0.5 μM or less, with respect to at least one cell line for a particular tumor. Exemplary cell lines for determining activity include human OVCAR-3 for tumors of the ovary, MCF-7 or MDA-MB-231 for breast tumors, HeLa for cervical tumors, PC3 or LNCap for tumors of the prostate, HepG2 for tumors of the liver, A549 or NCI-H226 for lung tumors, UMRC2 for kidney tumors, HT-29 or HCT116 colon tumors, PANC-1 for pancreatic tumors, U251 for brain tumors, MKN-45 for stomach tumors and SK-MEL-28 for melanoma.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The nucleoside compounds of the invention can be formulated as pharmaceutical compositions and administered to a subject in need of treatment, for example a mammal, such as a human patient, in a variety of forms adapted to the chosen route of administration, for example, orally or parenterally, by intravenous, intramuscular, topical or subcutaneous routes.

Thus, nucleoside compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the nucleoside compounds may be combined with one or more excipients and used in the form of ingestible tablets, buccal tablets, troches, capsules, elixirs, suspensions, syrups, wafers, and the like. The nucleoside compounds may be combined with a fine inert powdered carrier and inhaled by the subject or insufflated. Such compositions and preparations should contain at least 0.1% nucleoside compounds. The percentage of the compositions and preparations may, of course, be varied and may conveniently be between about 2% to about 60% of the weight of a given unit dosage form. The amount of nucleoside compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the nucleoside compounds may be incorporated into sustained-release preparations and devices.

The nucleoside compounds may also be administered intravenously or intraperitoneally by infusion or injection. Solutions of the nucleoside compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the nucleoside compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the nucleoside compounds in the required amount in the appropriate solvent with various of the other ingredients enumerated above, as required, followed by filter sterilization. In the case of sterile powders for the preparation of sterile injectable solutions the preferred methods of preparation are vacuum drying and freeze drying techniques, which yield a powder of the active ingredient plus any additional desired ingredient present in the previously sterile-filtered solutions.

For topical administration, the nucleoside compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the nucleoside compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the nucleoside compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of formula I or II can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the nucleoside compounds in a liquid composition, such as a lotion, will be from about 0.1-25% by weight, or from about 0.5-10% by weight. The concentration in a semi-solid or solid composition such as a gel or a powder can be about 0.1-5% by weight, or about 0.5-2.5% by weight.

The amount of the nucleoside compounds required for use in treatment will vary depending on the particular salt selected and with the route of administration, the nature of the condition being treated and the age and condition of the patient, and will be ultimately at the discretion of the attendant physician or clinician.

Effective dosages and routes of administration of agents of the invention are conventional. The exact amount (effective dose) of the nucleoside compound will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, 6 to 90 mg/kg/day, or in the range of 15 to 60 mg/kg/day. For example, suitable doses may be 0.5, 5, 10, 25, 50, 100, 250 or 500 mg/kg of body weight per day.

The nucleoside compounds are conveniently administered in unit dosage form; for example, containing 5 to 1000 mg, 10 to 750 mg, or 50 to 500 mg of active ingredient per unit dosage form.

The nucleoside compounds can be administered to achieve peak plasma concentrations of from about 0.5 to about 75 µM, about 1 to 50 µM, or, about 2 to about 30 µM. Exemplary desirable plasma concentrations include at least or no more than 0.25, 0.5, 1, 5, 10, 25, 50, 75, 100 or 200 µM. This may be achieved, for example, by the intravenous injection of a 0.05 to 5% solution of the nucleoside compounds, optionally in saline, or orally administered as a bolus containing about 1-100 mg of the nucleoside compounds. Desirable blood levels may be maintained by continuous infusion to provide about 0.01-5.0 mg/kg/hr, for example at least or no more than 0.005, 0.01, 0.1, 2.5, 5.0 or 10.0 mg/kg/hr. Alternatively, such levels can be obtained by intermittent infusions containing about 0.4-15 mg/kg, for example at least or no more than 0.25, 0.5, 1.0, 5.0, 10.0, 15.0 or 25.0 mg/kg of the nucleoside compounds.

The nucleoside compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Targeting Nucleosides to Cells

In an exemplary embodiment, the nucleoside compound is targeted to cells where treatment is desired, for example, to human cancer cells. The compound is targeted to the desired cell by conjugation to a targeting moiety that specifically binds the desired cell, thereby directing administration of a conjugated molecule. Useful targeting moieties are ligands which specifically bind cell antigens or cell surface ligands, for example, antibodies against the B cell antigen, CD19 (such as B43) and the like.

To form the conjugates of the invention, targeting moieties are covalently bonded to sites on the nucleoside compound. The targeting moiety, which is often a polypeptide molecule, is bound to compounds of the invention at reactive sites, including $NH_2$, SH, CHO, COOH, and the like. Specific linking agents are used to join the compounds. Linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et al., Bioconjugate Techniques, Academic Press, 1996; Hermanson, et al., Immobilized Affinity Ligand Techniques, Academic Press, 1992; and Pierce Catalog and Handbook, 1996, pp. T155-T201.

EXAMPLES

The invention may be further clarified by reference to the following Examples, which serve to exemplify some of the preferred embodiments, and not to limit the invention in any way.

Examples 1-2

Synthesis of Nucleoside Derivatives

All the anhydrous solvents such as acetonitrile, methanol, ethanol, ethyl acetate, tetrahydrofuran, chloroform, and methylene chloride were distilled over $CaH_2$ or $P_2O_5$ or Na/benzophenone prior to use. All chemicals were reagent grade and were purchased from Aldrich Chemical Company (Milwaukee, Wis.) or Sigma Chemical Company (St. Louis, Mo.).

Physical Characteristics

Proton NMR spectra were recorded on a Varian-400 MHz spectrometer in deuterated solvents such as DMSO-$d_6$, CDCl$_3$, acetonitrile-$d_3$ or acetone-$d_6$. Chemical shifts are reported in parts per million (ppm) with tetramethylsilane (TMS) as an internal standard at zero ppm. Coupling constants (J) are given in hertz and the abbreviations s, d, t, q, and m refer to singlet, doublet, triplet, quartet and multiplet, respectively. TLC was performed on Merck precoated 60$F_{254}$ plates. Column chromatography was performed using silica gel 60 (230-400 mesh, Merck).

Example 1

Synthesis of Substituted Fluorocyclopentenol

A suitably substituted fluorocyclopentenol was prepared from isopropylide-D-ribose 1 as outlined in Scheme 1.

An important intermediate in the synthesis is the tertiary allylic β-alcohol 6. The corresponding α epimer is resistant to oxidation, and thus hinders the formation of intermediate 7. The intermediate tertiary allylic β-alcohol 6 is selectively prepared from its open ring counterpart, intermediate 5. It was found that the presence of bulky protecting groups on the primary alcohol favors formation of compound 5 over its diastereomeric epimer, thus facilitating preparation of intermediate tertiary allylic β-alcohol 6 and, ultimately, the oxidized product 7. In this regard, the benzyl protecting group gave the wrong α-epimer, the tert-butyldimethyl silyl protecting group showed some selectivity (about 75:8 β:α), the tert-butyldiphenyl silyl protecting group showed a better yield and even higher selectivity and the trityl group provided high yield and high stereoselectivity.

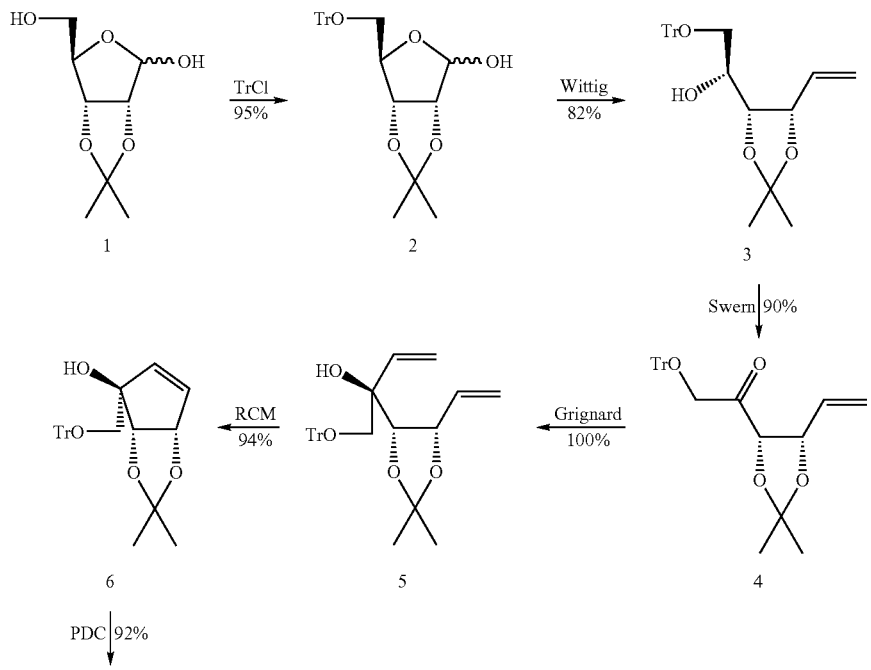

Scheme 1

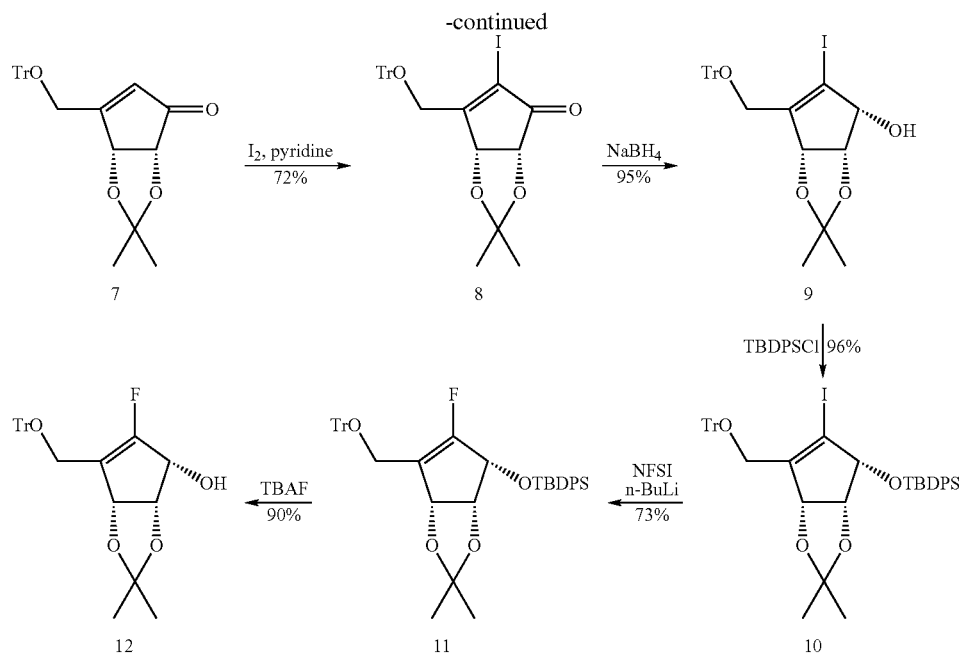

2,3-O-Isopropylidene-5-trityl-D-ribose (2)

A solution of isopropylidene-D-ribose 1 (10 g, 52.58 mmol) and trityl chloride (21.95 g, 78.88 mmol) in pyridine (250 ml) was stirred at room temperature for 20 hours. After water was added, the reaction mixture was extracted with ethyl acetate, dried, filtered, and evaporated in vacuo. The resulting residue was purified by silica gel column chromatography using hexane and ethyl acetate (4:1) as the eluent to give trityl ether 2 (21.53 g, 95%) as a colorless oil; $^1$H NMR (400 MHz, CDCl$_3$) δ 7.40-7.21 (m, 15H), 5.72 (d, J=4.0 Hz, 0.4H), 5.32 (s, 0.6H), 4.76 (d, J=5.6 Hz, 0.6H), 4.72 (dd, J=6.0, 4.0 Hz, 0.4H), 4.63 (d, J=6.0 Hz, 0.6H), 4.57 (dd, J=6.4, 1.2 Hz, 0.4H), 4.34-4.33 (m, 0.6H), 4.18-4.17 (m, 0.4H), 4.09 (bs, 2H), 3.40 (dd, J=10.4, 2.8 Hz, 0.4H), 3.39 (dd, J=10.0, 3.6 Hz, 0.6H), 3.32 (dd, J=10.0, 3.6 Hz, 0.6H), 3.00 (dd, J=10.4, 3.2 Hz, 0.4H), 1.53 (s, 1.2H), 1.46 (s, 1.8H), 1.35 (s, 1.2H), 1.32 (s, 1.8H).

(1R)-1-((4R,5S)-2,2-Dimethyl-5-vinyl-[1,3]dioxolan-4-yl)-2-trityloxy-ethanol (3)

To a stirred suspension of methyl triphenylphosphonium bromide (32.28 g, 90.36 mmol) in tetrahydrofuran (300 ml) was added potassium tert-butoxide (10.79 g, 88.26 mmol, the purity of reagent: 95%) at 0° C., and the mixture was stirred at room temperature for 1 hour. After the mixture was cooled again to 0° C., a solution of lactol 2 (18.18 g, 42.03 mmol) in tetrahydrofuran (50 ml) was added. The reaction mixture was stirred at 0° C. for 3 hours, and at room temperature for 4 hours. The reaction mixture was partitioned between water and ethyl acetate, washed with brine, dried, filtered, and evaporated in vacuo. The resulting residue was purified by silica gel column chromatography using hexane and ethyl acetate (8:1) as the eluent to give olefin 3 (15.20 g, 82%) as a white solid; $^1$H NMR (400 MHz, CDCl$_3$) δ 7.45-7.21 (m, 15H), 5.96 (td, J=10.4, 6.8 Hz, 1H), 5.37 (td, J=16.8, 1.6 Hz, 1H), 5.23 (td, J=10.8, 1.6 Hz, 1H), 4.67 (t, J=6.4, 1H), 4.15 (dd, J=8.8, 6.4 Hz, 1H), 3.77-3.71 (m, 1H), 3.36 (dd, J=9.6, 3.6 Hz, 1H), 3.32 (dd, J=9.6, 6.0 Hz, 1H), 2.37 (d, J=4.8 Hz, 1H), 1.36 (s, 3H), 1.34 (s, 3H).

1-((4S,5S)-2,2-Dimethyl-5-vinyl-[1,3]dioxolan-4-yl)-2-trityloxy-ethanone (4)

To a stirred solution of (COCl)$_2$ (28.69 ml, 57.38 mmol, 2 M solution in CH$_2$Cl$_2$) in CH$_2$Cl$_2$ (200 ml) was dropwise added a solution of DMSO (8.9 ml, 125.51 mmol) in CH$_2$Cl$_2$ (30 ml) at −78° C., and the reaction mixture was stirred at the same temperature for 30 minutes. A solution of alcohol 3 (15.44 g, 35.86 mmol) in CH$_2$Cl$_2$ (30 ml) was added and the reaction mixture was stirred at −78° C. for 1 hour. Triethylamine (32.99 ml, 236.68 mmol) was added at −78° C. and then the reaction mixture was allowed to warm to room temperature and stirred for 1 hour. A saturated ammonium chloride solution was added carefully at 0° C. and the reaction mixture partitioned between CH$_2$Cl$_2$ and water. The organic layer was dried, filtered, and evaporated under reduced pressure. The residue was purified by silica gel column chromatography using hexane and ethyl acetate (6:1) to give ketone 4 (13.83 g, 90%) as a white solid; $^1$H NMR (400 MHz, CDCl$_3$) δ 7.46-7.23 (m, 15H), 5.56 (ddd, J=17.2, 10.4, 6.8 Hz, 1H), 5.26 (td, J=16.8, 1.2 Hz, 1H), 5.13 (td, J=10.4, 1.2 Hz, 1H), 4.88-4.84 (m, 1H), 4.76 (d, J=7.6 Hz, 1H), 4.06 (d, J=18.0 Hz, 1H), 3.72 (d, J=18.4 Hz, 1H), 1.41 (s, 3H), 1.34 (s, 3H).

(2R)-2-((4S,5S)-2,2-Dimethyl-5-vinyl-[1,3]dioxolan-4-yl)-1-trityloxy-but-3-en-2-ol (5)

To a stirred solution of 4 (14.66 g, 34.22 mmol) in tetrahydrofuran (150 ml) was added dropwise vinylmagnesium bromide (68.44 ml, 68.44 mmol, 1.0 M solution in tetrahydrofuran) at −78° C., and the reaction mixture was stirred for 1 hour at the same temperature. The reaction mixture was quenched by saturated ammonium chloride solution and brine, and extracted with ethyl acetate. The organic layer was dried over anhydrous magnesium sulfate, filtered, and evaporated. The resulting oil was purified by column chromatography (hexane:ethyl acetate=9:1) to give 5 (15.62 g, 100%) as a white semi-solid; $^1$H NMR (400 MHz, CDCl$_3$) δ 7.43-7.22 (m, 15H), 6.16 (dd, J=17.2, 10.8 Hz, 1H), 6.01-5.93 (m, 1H), 5.42 (dd, J=17.2, 1.2 Hz, 1H), 5.27 (dd, J=10.8, 1.2 Hz, 1H), 4.99 (d, J=16.0 Hz, 1H), 4.98 (d, J=11.2 Hz, 1H), 4.54-4.47 (m, 2H), 3.33 (d, J=8.8 Hz, 1H), 3.05 (d, J=8.4 Hz, 1H), 2.54 (bs, 1H), 1.46 (s, 3H), 1.40 (s, 3H).

(3aS,4R,6aS)-2,2-Dimethyl-4-trityloxymethyl-4,6a-dihydro-3aH-cyclopenta[1,3]dioxol-4-ol (6)

To a stirred solution of 5 (14.55 g, 31.86 mmol) in methylene chloride (100 ml) was added tricyclohexylphosphine [1,3-bis(2,4,6-trimethylphenyl)-4,5-dihydroimidazol-2-ylidene]-[benzylidine]ruthenium (VI) dichloride (270 mg, 0.32 mmol), and the reaction mixture was stirred at room temperature for 2 days. The volatiles were removed under reduced pressure and the residue was purified by silica gel column chromatography (hexane:ethyl acetate=5:1) to give 6 (12.83 g, 94%) as a white semi-solid; $^1$H NMR (400 MHz, CDCl$_3$) δ 7.47-7.21 (m, 15H), 5.93 (dd, J=5.6, 1.6 Hz, 1H), 5.73 (d, J=5.6 Hz, 1H), 5.31 (d, J=5.6 Hz, 1H), 4.56 (d, J=5.6 Hz, 1H), 3.59 (d, J=9.2 Hz, 1H), 3.15 (d, J=9.2 Hz, 1H), 3.02 (s, 1H), 1.32 (s, 3H), 1.21 (s, 3H).

(3R,6aR)-2,2-Dimethyl-6-trityloxymethyl-3a,6a-dihydro-cyclopenta[1,3]dioxol-4-one (7)

A solution of 6 (12.17 g, 28.40 mmol), 4 Å molecular sieves (14.2 g), and pyridinium dichromate (32.05 g, 85.20 mmol) in DMF (100 ml) was stirred at room temperature for 2 days. After the mixture was diluted with diethyl ether and ethyl acetate, the mixture was filtered through a short pad of a mixture of silica gel and Celite. The filtrate was evaporated and the resulting residue was purified by silica gel column chromatography (hexane:ethyl acetate=4:1) to give ketone 7 (11.14 g, 92%) as a white solid; $^1$H NMR (400 MHz, CDCl$_3$) δ 7.44-7.22 (m, 15H), 6.42 (t, J=2.0 Hz, 1H), 4.96 (d, J=5.2 Hz, 1H), 4.45 (d, J=5.6 Hz, 1H), 4.23 (dd, J=18.4, 2.0 Hz, 1H), 3.93 (dd, J=18.0, 2.0 Hz, 1H), 1.34 (s, 6H).

(3R,6aR)-5-Iodo-2,2-dimethyl-6-trityloxymethyl-3a,6a-dihydro-cyclopenta[1,3]dioxol-4-one (8)

To a stirred solution of 7 (17.19 g, 40.30 mmol) and iodine (12.27 g, 48.36 mmol) in methylene chloride (80 ml) was added pyridine (3.0 ml, 36.27 mmol) under nitrogen atmosphere at 0° C., and the reaction mixture was stirred at room temperature for 6 hours. The mixture was diluted with methylene chloride and water and the organic layer was washed with water, saturated sodium thiosulfate solution, brine, and dried over anhydrous magnesium sulfate. After evaporation of solvents, the residue was purified by flash silica gel column chromatography (hexane:ethyl acetate=7:1) to afford 8 (16.03 g, 72%) as a white solid; $^1$H NMR (400 MHz, CDCl$_3$) δ 7.43-7.15 (m, 15H), 5.35 (d, J=5.6 Hz, 1H), 4.45 (d, J=5.6 Hz, 1H), 4.19 (d, J=16.0 Hz, 1H), 4.08 (d, J=16.0 Hz, 1H), 1.36 (s, 3H), 1.24 (s, 3H).

(3R,4R,6aR)-5-Iodo-2,2-dimethyl-6-trityloxymethyl-4,6a-dihydro-3aH-cyclopenta[1,3]dioxol-4-ol (9)

To a stirred solution of 8 (8.97 g, 16.25 mmol) and cerium (III) chloride heptahydrate (6.66 g, 17.88 mmol) in methanol (80 ml) was added sodium borohydride (676 mg, 17.88 mmol) at 0° C. and the mixture was stirred at the same temperature for 1 hour. The mixture was diluted with brine and extracted with ethyl acetate. The organic layer was washed with brine, dried over anhydrous magnesium sulfate, and evaporated. The residue was purified by flash silica gel column chromatography (hexane:ethyl acetate=6:1) to afford 9 (8.56 g, 95%) as a white solid; $^1$H NMR (400 MHz, CDCl$_3$) δ 7.48-7.20 (m, 15H), 5.20 (d, J=5.6 Hz, 1H), 4.76 (t, J=5.6 Hz, 1H), 3.88 (d, J=12.0 Hz, 1H), 3.79 (d, J=12.0 Hz, 1H), 2.78 (d, J=10.4 Hz, 1H), 1.40 (s, 3H), 1.30 (s, 3H).

(3R,4R,6aR)-tert-Butyl-(5-iodo-2,2-dimethyl-6-trityloxymethyl-4,6a-dihydro-3aH-cyclopenta[1,3]dioxol-4-yloxy)-diphenyl-silane (10)

To a stirred solution of 9 (8.53 g, 15.39 mmol) and imidazole (3.14 g, 46.17 mmol) in anhydrous N,N-dimethylformamide (70 ml) was added TBDPSCl (4.80 ml, 18.47 mmol) at room temperature under nitrogen atmosphere and the reaction mixture was stirred at the same temperature overnight. The mixture was quenched with water, extracted with diethyl ether, dried over anhydrous magnesium sulfate, and evaporated. The residue was purified by flash silica gel column chromatography (hexane:ethyl acetate=30:1) to afford 10 (11.66 g, 96%) as a colorless oil; $^1$H NMR (400 MHz, CDCl$_3$) δ 7.82-7.18 (m, 25H), 4.94 (d, J=5.6 Hz, 1H), 4.47 (d, J=5.6 Hz, 1H), 4.05 (d, J=5.6 Hz, 1H), 3.89 (d, J=12.0 Hz, 1H), 3.78 (d, J=12.0 Hz, 1H), 1.29 (s, 3H), 1.25 (s, 3H), 1.13 (s, 9H).

(3R,4R,6aR)-tert-Butyl-(5-fluoro-2,2-dimethyl-6-trityloxymethyl-4,6a-dihydro-3aH-cyclopenta[1,3]dioxol-4-yloxy)-diphenyl-silane (11)

To a stirred solution of 10 (11.66 g, 14.71 mmol) and N-fluorobenzenesulfonimide (5.566 g, 17.65 mmol) in dry tetrahydrofuran (100 ml) was slowly added n-butyllithium (27.6 ml, 44.13 mmol, 1.6 M solution in hexanes) at −78° C. under nitrogen atmosphere and the reaction mixture was stirred at the same temperature for 1 hour. The mixture was quenched with saturated ammonium chloride solution and extracted with ethyl acetate. The organic layer was dried over anhydrous magnesium sulfate, and evaporated. The residue was purified by flash silica gel column chromatography (hexane:ethyl acetate=6:1) to afford 11 (7.35 g, 73%) as a white solid; $^1$H NMR (400 MHz, CDCl$_3$) δ 7.81-7.17 (m, 25H), 4.94 (t, J=7.2 Hz, 1H), 4.35 (m, 1H), 4.25 (m, 1H), 3.89 (t, J=12.0 Hz, 1H), 3.77 (t, J=12.0 Hz, 1H), 1.42 (s, 3H), 1.38 (s, 3H), 1.08 (s, 9H).

(3R,4R,6aR)-5-Fluoro-2,2-dimethyl-6-trityloxymethyl-4,6a-dihydro-3aH-cyclopenta[1,3]dioxol-4-ol (12)

To a stirred solution of 11 (7.35 g, 10.73 mmol) in tetrahydrofuran (50 ml) was added dropwise tetra-n-butylammonium fluoride (12.88 ml, 12.88 mmol, 1.0 M in tetrahydrofuran) and the mixture was stirred at room temperature for 1 hour. After the removal of solvent, the residue was purified by flash silica gel column chromatography (hexane:ethyl acetate=4:1) to afford 12 (4.31 g, 90%) as a colorless oil; $^1$H NMR (400 MHz, CDCl$_3$) δ 7.43-7.18 (m, 15H), 5.12 (t, J=5.6 Hz, 1H), 4.69 (m, 1H), 4.38 (t, J=5.6 Hz, 1H), 3.91 (d, J=13.2 Hz, 1H), 3.74 (d, J=13.2 Hz, 1H), 2.75 (d, J=10.4 Hz, 1H), 1.43 (s, 3H), 1.39 (s, 3H).

Example 2

Synthesis of 2-fluoro cyclopentenyl nucleosides

The fluoro-cyclopentenol 12 was coupled to a protected $N^3$-benzoylbase, as outlined in Scheme 2.

General Procedure for Base Condensation

A solution of diethylazodicarboxylate (780 mg, 4.48 mmol) in dry tetrahydrofuran (30 ml) was added dropwise to a solution of the fluoro-cyclopentenol 12 (800 mg, 1.79 mmol), triphenylphosphine (1174.8 mg, 4.48 mmol), and a selected $N^3$-benzoylbase (uracil derivatives, 3.58 mmol) in dry tetrahydrofuran (10 ml) at 0° C. under nitrogen atmosphere. The reaction mixture was stirred at room temperature for 15 hours, and then the volatiles were evaporated under reduced pressure. The residue was purified by flash silica gel column chromatography (hexane:ethyl acetate=4:1) to give the base-condensed product.

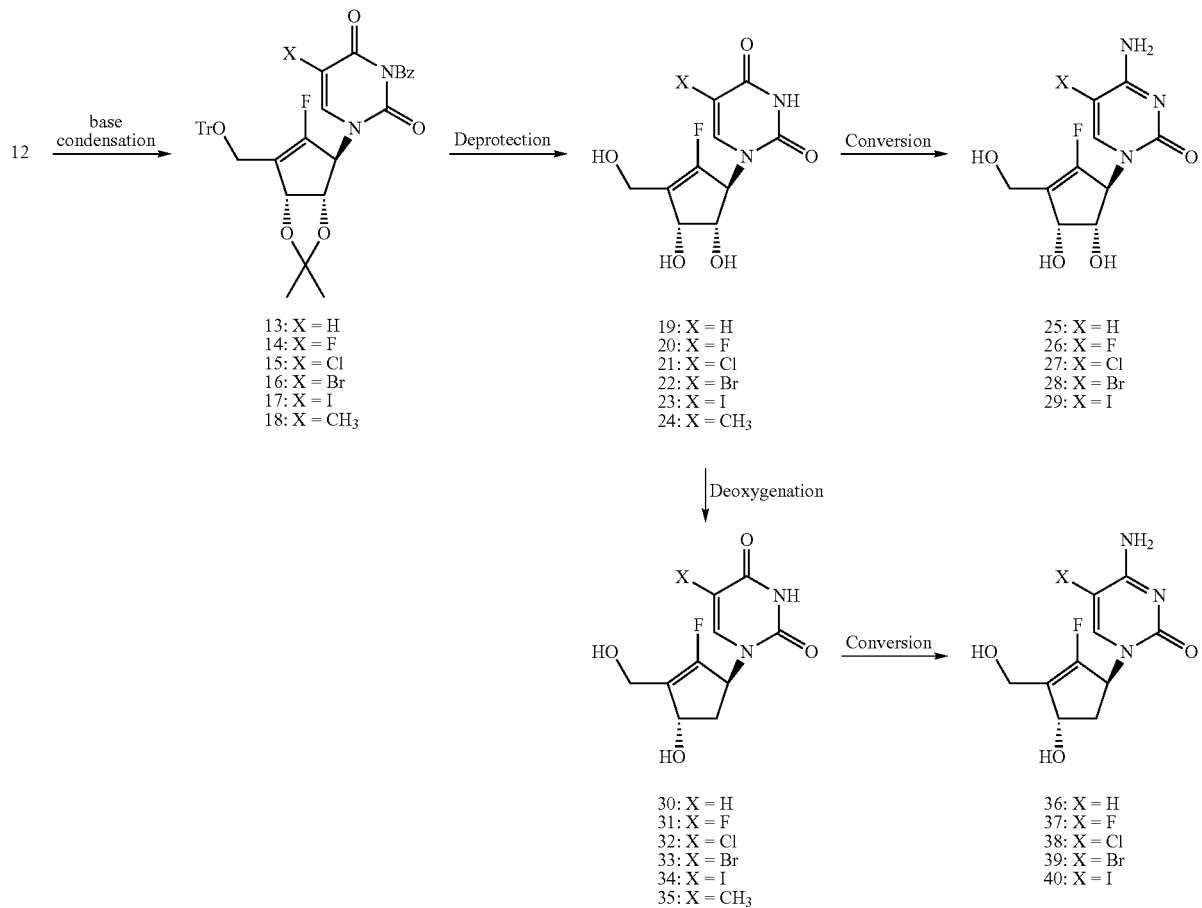

Scheme 2

Yield and spectroscopic data for the condensation products 13-18 was as follows:

(3R,4S,6aR)-3-Benzoyl-1-(5-fluoro-2,2-dimethyl-6-trityloxymethyl-4,6a-dihydro-3aH-cyclopenta[1,3]dioxol-4-yl)-1H-pyrimidine-2,4-dione (13). 865.5 mg, 75%; $^1$H NMR (400 MHz, CDCl$_3$) δ 7.97-7.24 (m, 15H), 7.66 (d, J=8.0 Hz, 1H), 5.92 (d, J=8.0 Hz, 1H), 5.49 (bs, 1H), 4.72 (t, J=6.0 Hz, 1H), 4.35 (d, J=13.2 Hz, 1H), 4.29 (t, J=6.0 Hz, 1H), 4.15 (dt, J=13.2, 2.4 Hz, 1H), 1.43 (s, 3H), 1.34 (s, 3H).

(3R,4S,6aR)-3-Benzoyl-1-(5-fluoro-2,2-dimethyl-6-trityloxymethyl-4,6a-dihydro-3aH-cyclopenta[1,3]dioxol-4-yl)-5-fluoro-1H-pyrimidine-2,4-dione (14). 924.6 mg, 78%; $^1$H NMR (400 MHz, CDCl$_3$) δ 7.94-7.24 (m, 15H), 7.13 (d, J=5.2 Hz, 1H), 5.33 (td, J=6.0, 0.8 Hz, 1H), 5.27 (bs, 1H), 4.62 (t, J=7.2 Hz, 1H), 4.03 (d, J=12.8 Hz, 1H), 3.87 (dt, J=12.8, 2.4 Hz, 1H), 1.44 (s, 3H), 1.36 (s, 3H).

(3R,4S,6aR)-3-Benzoyl-5-chloro-1-(5-fluoro-2,2-dimethyl-6-trityloxymethyl-4,6a-dihydro-3aH-cyclopenta[1,3]dioxol-4-yl)-1H-pyrimidine-2,4-dione (15). 875.3 mg, 72%; $^1$H NMR (400 MHz, CDCl$_3$) δ 7.95-7.21 (m, 15H), 7.83 (s, 1H), 5.42 (td, J=6.0, 0.8 Hz, 1H), 5.35 (bs, 1H), 4.65 (t, J=7.2 Hz, 1H), 3.99 (d, J=12.8 Hz, 1H), 3.75 (dt, J=12.8, 2.4 Hz, 1H), 1.43 (s, 3H), 1.32 (s, 3H).

(3R,4S,6aR)-3-Benzoyl-5-bromo-1-(5-fluoro-2,2-dimethyl-6-trityloxymethyl-4,6a-dihydro-3aH-cyclopenta[1,3]dioxol-4-yl)-1H-pyrimidine-2,4-dione (16). 893.7 mg, 69%; $^1$H NMR (400 MHz, CDCl$_3$) δ 8.04 (s, 1H), 7.97-7.28 (m, 15H), 5.29 (td, J=6.0, 0.8 Hz, 1H), 5.25 (bs, 1H), 4.71 (t, J=7.2 Hz, 1H), 4.15 (d, J=12.8 Hz, 1H), 3.95 (dt, J=12.8, 2.4 Hz, 1H), 1.41 (s, 3H), 1.37 (s, 3H).

(3R,4S,6aR)-3-Benzoyl-1-(5-fluoro-2,2-dimethyl-6-trityloxymethyl-4,6a-dihydro-3aH-cyclopenta[1,3]dioxol-4-yl)-5-iodo-1H-pyrimidine-2,4-dione (17). 855.2 mg, 62%; $^1$H NMR (400 MHz, CDCl$_3$) δ 8.26 (s, 1H), 7.93-7.22 (m, 15H), 5.38 (td, J=6.0, 0.8 Hz, 1H), 5.29 (bs, 1H), 4.73 (t, J=7.2 Hz, 1H), 4.14 (d, J=12.8 Hz, 1H), 3.97 (dt, J=12.8, 2.4 Hz, 1H), 1.48 (s, 3H), 1.34 (s, 3H).

(3R,4S,6aR)-3-Benzoyl-1-(5-fluoro-2,2-dimethyl-6-trityloxymethyl-4,6a-dihydro-3aH-cyclopenta[1,3]dioxol-4-yl)-5-methyl-1H-pyrimidine-2,4-dione (18). 990.4 mg, 84%; $^1$H NMR (400 MHz, CDCl$_3$) δ 7.94-7.22 (m, 15H), 7.25 (s, 1H), 5.43 (td, J=6.0, 0.8 Hz, 1H), 5.19 (bs, 1H), 4.52 (t, J=7.2 Hz, 1H), 4.13 (d, J=12.8 Hz, 1H), 4.01 (dt, J=12.8, 2.4 Hz, 1H), 2.02 (s, 3H), 1.44 (s, 3H), 1.36 (s, 3H).

General Procedure for the Deprotection

A protected compound 13-18 (1.00 mmol) was dissolved in 10 ml of 1N HCl/methanol (2:1, v/v) and the reaction mixture stirred at room temperature for 20 hours. The solvent was removed under reduced pressure, and the resulting residue was purified by flash silica gel column chromatography (methylene chloride:methanol=10:1) to give an N-benzoyl uracil derivative.

The N-benzoyl uracil derivative obtained above was treated with 10 ml of methanolic ammonia, and the mixture was stirred in a sealed tube at room temperature overnight. The reaction mixture was evaporated and the residue was purified by flash silica gel column chromatography (methylene chloride:methanol=5:1) to give a uracil derivative of Table 1, which was crystallized from diethyl ether/methanol.

TABLE 1

Uracil Derivatives

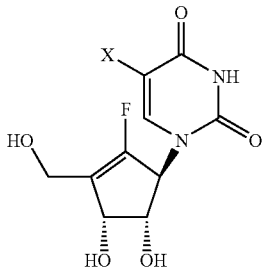

| No | Name | X | Formula | MW |
|---|---|---|---|---|
| 19 | RX-3116 | H | C$_{10}$H$_{11}$FN$_2$O$_5$ | 258.2 |
| 20 | RX-3116A | F | C$_{10}$H$_{10}$F$_2$N$_2$O$_5$ | 276.2 |
| 21 | RX-3116B | Cl | C$_{10}$H$_{10}$ClFN$_2$O$_5$ | 292.7 |
| 22 | RX-3116C | Br | C$_{10}$H$_{10}$BrFN$_2$O$_5$ | 337.1 |
| 23 | RX-3116D | I | C$_{10}$H$_{10}$FIN$_2$O$_5$ | 384.1 |
| 24 | RX-3116E | CH$_3$ | C$_{11}$H$_{13}$FN$_2$O$_5$ | 272.2 |

Yield and spectroscopic date for the uracil derivatives 19-24 was as follows:

(1S,4R,5S)-1-(2-Fluoro-4,5-dihydroxy-3-hydroxymethyl-cyclopent-2-enyl)-1H-pyrimidine-2,4-dione (19, RX-3116). 170.4 mg, 66%; $^1$H NMR (400 MHz, CD$_3$OD) δ 7.48 (d, J=8.0 Hz, 1H), 5.74 (d, J=8.0 Hz, 1H), 5.44 (bs, 1H), 4.68 (t, J=5.2 Hz, 1H), 4.37 (d, J=12.8 Hz, 1H), 4.20 (td, J=5.6, 0.8 Hz, 1H), 4.12 (dt, J=12.8, 2.4 Hz, 1H).

(1S,4R,5S)-5-Fluoro-1-(2-fluoro-4,5-dihydroxy-3-hydroxymethyl-cyclopent-2-enyl)-1H-pyrimidine-2,4-dione (20, RX-3116A). 168.5 mg, 61%; $^1$H NMR (400 MHz, CD$_3$OD) δ 7.74 (dd, J=6.4, 0.8 Hz, 1H), 5.46 (bs, 1H), 4.67 (td, J=5.6, 1.2 Hz, 1H), 4.37 (d, J=12.8 Hz, 1H), 4.18 (td, J=5.6, 1.2 Hz, 1H), 4.12 (dt, J=12.8, 2.4 Hz, 1H).

(1S,4R,5S)-5-Chloro-1-(2-fluoro-4,5-dihydroxy-3-hydroxymethyl-cyclopent-2-enyl)-1H-pyrimidine-2,4-dione (21, RX-3116B). 190.2 mg, 65%; $^1$H NMR (400 MHz, CD$_3$OD) δ 8.43 (s, 1H), 5.45 (bs, 1H), 4.69 (td, J=5.6, 1.2 Hz, 1H), 4.35 (d, J=12.8 Hz, 1H), 4.20 (td, J=5.6, 1.2 Hz, 1H), 4.15 (dt, J=12.8, 2.4 Hz, 1H).

(1S,4R,5S)-5-Bromo-1-(2-fluoro-4,5-dihydroxy-3-hydroxymethyl-cyclopent-2-enyl)-1H-pyrimidine-2,4-dione (22, RX-3116C). 192.1 mg, 57%; $^1$H NMR (400 MHz, CD$_3$OD) δ 8.59 (s, 1H), 5.43 (bs, 1H), 4.64 (td, J=5.6, 0.8 Hz, 1H), 4.35 (d, J=12.8 Hz, 1H), 4.16 (td, J=5.6, 0.8 Hz, 1H), 4.11 (dt, J=12.8, 2.4 Hz, 1H).

(1S,4R,5S)-1-(2-Fluoro-4,5-dihydroxy-3-hydroxymethyl-cyclopent-2-enyl)-5-iodo-1H-pyrimidine-2,4-dione (23, RX-3116D). 195.9 mg, 51%; $^1$H NMR (400 MHz, CD$_3$OD) δ 8.67 (s, 1H), 5.46 (bs, 1H), 4.66 (td, J=5.6, 1.2 Hz, 1H), 4.36 (d, J=12.8 Hz, 1H), 4.15 (td, J=5.6, 1.2 Hz, 1H), 4.08 (dt, J=12.8, 2.4 Hz, 1H).

(1S,4R,5S)-1-(2-Fluoro-4,5-dihydroxy-3-hydroxymethyl-cyclopent-2-enyl)-5-methyl-1H-pyrimidine-2,4-dione (24, RX-3116E). 204.2 mg, 75%; $^1$H NMR (400 MHz, CD$_3$OD) δ 7.62 (s, 1H), 5.49 (bs, 1H), 4.69 (td, J=5.6, 1.2 Hz, 1H), 4.36 (d, J=13.2 Hz, 1H), 4.17 (td, J=5.6, 1.2 Hz, 1H), 4.10 (dt, J=13.2, 2.4 Hz, 1H), 1.82 (s, 3H).

General Procedure for the Conversion to Cytosine Derivatives

A solution of a uracil compound 19-24 from Table 1 (1.00 mmol) in anhydrous pyridine (10 ml) was treated with acetic anhydride (940 μl, 10.0 mmol), and the mixture stirred at ambient temperature for 5 hours. The residue obtained after evaporation of all the volatiles was diluted with methylene chloride; washed with diluted HCl, saturated NaHCO$_3$ solution and brine; dried (MgSO$_4$); filtered, and evaporated. The residue containing the triacetate was used in the next step without further purification.

A solution of 1,2,4-triazole (760 mg, 11.0 mmol) and phosphorous oxychloride (915 μl, 10.0 mmol) in acetonitrile (10 ml) was treated with triethylamine (1.25 ml, 9.0 mmol) and triacetate (1.00 mmol) in 4 ml of acetonitrile. The reaction mixture was stirred at room temperature for 15 hours. Additional triethylamine (1.5 ml) and water (4.5 ml) were added, and the mixture was stirred for 10 minutes. After dilution with methylene chloride, the mixture was washed with saturated NaHCO$_3$ solution and brine, dried (MgSO$_4$), filtered, and evaporated. The residue was used in the next step without further purification.

To a solution above residue in 1,4-dioxane (8 ml) ammonium hydroxide (28%, 2 ml) was added at 0° C., and the reaction mixture was stirred at ambient temperature for 10 hours. After removal of all volatiles, the residue was dissolved in methanolic ammonia (5 ml) and stirred at ambient temperature for 12 hours. The reaction mixture was evaporated, and the residue was purified by ODS column chromatography (water:acetone=20:1) to give the cytosine derivative of Table 2, which was crystallized from diethyl ether/methanol.

TABLE 2

Cytosine Derivatives

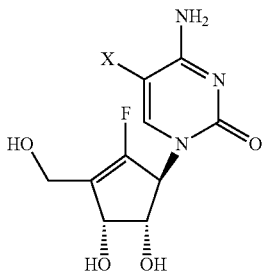

| No | Name | X | Formula | MW |
|----|------|---|---------|-----|
| 25 | RX-3117 | H | $C_{10}H_{12}FN_3O_4$ | 257.2 |
| 26 | RX-3117A | F | $C_{10}H_{11}F_2N_3O_4$ | 275.2 |
| 27 | RX-3117B | Cl | $C_{10}H_{11}ClFN_3O_4$ | 291.7 |
| 28 | RX-3117C | Br | $C_{10}H_{11}BrFN_3O_4$ | 336.1 |
| 29 | RX-3117D | I | $C_{10}H_{11}FN_3O_4$ | 383.1 |

Yield and spectroscopic data for cytosine derivatives 25-29 were as follows:

(1S,4R,5S)-4-Amino-1-(2-fluoro-4,5-dihydroxy-3-hydroxymethyl-cyclopent-2-enyl)-1H-pyrimidin-2-one (25, RX-3117). 133.8 mg, 52%; $^1$H NMR (400 MHz, CD$_3$OD) δ 7.47 (d, J=7.6 Hz, 1H), 5.92 (d, J=7.6 Hz, 1H), 5.35 (bs, 1H), 4.69 (t, J=5.6 Hz, 1H), 4.36 (d, J=12.8 Hz, 1H), 4.26 (td, J=5.6, 0.8 Hz, 1H), 4.11 (dt, J=12.8, 2.4 Hz, 1H).

(1S,4R,5S)-4-Amino-5-fluoro-1-(2-fluoro-4,5-dihydroxy-3-hydroxymethyl-cyclopent-2-enyl)-1H-pyrimidin-2-one (26, RX-3117A). 156.9 mg, 57%; $^1$H NMR (400 MHz, CD$_3$OD) δ 7.79 (d, J=6.4 Hz, 1H), 5.41 (bs, 1H), 4.68 (td, J=5.6, 1.2 Hz, 1H), 4.37 (d, J=12.8 Hz, 1H), 4.23 (td, J=5.6, 1.2 Hz, 1H), 4.12 (dt, J=12.8, 2.4 Hz, 1H).

(1S,4R,5S)-4-Amino-5-chloro-1-(2-fluoro-4,5-dihydroxy-3-hydroxymethyl-cyclopent-2-enyl)-1H-pyrimidin-2-one (27, RX-3117B). 134.2 mg, 46%; $^1$H NMR (400 MHz, CD$_3$OD) δ 8.50 (s, 1H), 5.37 (bs, 1H), 4.70 (td, J=5.6, 1.2 Hz, 1H), 4.41 (d, J=12.8 Hz, 1H), 4.25 (td, J=5.6, 1.2 Hz, 1H), 4.17 (dt, J=12.8, 2.4 Hz, 1H).

(1S,4R,5S)-4-Amino-5-bromo-1-(2-fluoro-4,5-dihydroxy-3-hydroxymethyl-cyclopent-2-enyl)-1H-pyrimidin-2-one (28, RX-3117C). 164.7 mg, 49%; $^1$H NMR (400 MHz, CD$_3$OD) δ 8.62 (s, 1H), 5.41 (bs, 1H), 4.69 (td, J=5.6, 1.2 Hz, 1H), 4.40 (d, J=12.8 Hz, 1H), 4.22 (td, J=5.6, 1.2 Hz, 1H), 4.14 (dt, J=12.8, 2.4 Hz, 1H).

(1S,4R,5S)-4-Amino-1-(2-fluoro-4,5-dihydroxy-3-hydroxymethyl-cyclopent-2-enyl)-5-iodo-1H-pyrimidin-2-one (29, RX-3117D). 160.9 mg, 42%; $^1$H NMR (400 MHz, CD$_3$OD) δ 8.70 (s, 1H), 5.43 (bs, 1H), 4.66 (td, J=5.6, 0.8 Hz, 1H), 4.34 (d, J=12.8 Hz, 1H), 4.21 (td, J=5.6, 0.8 Hz, 1H), 4.08 (dt, J=12.8, 2.4 Hz, 1H).

General Procedure for the Deoxygenation

To a stirred solution of a uracil derivative of Table 1 (0.50 mmol) in pyridine (5 ml) was added DMAP (1.00 mmol) and 1,3-dichloro-1,1,3,3-tetraisopropyldisiloxane (0.75 mmol) at ambient temperature. After 10 hours later, the solvent was removed, and the residue was partitioned between methylene chloride and water. The organic layer was washed with brine and then dried over anhydrous magnesium sulfate. The solvent was removed under reduced pressure and the crude residue was used in the next step without further purification.

To a stirred solution of the crude residue in anhydrous acetonitrile (5 ml) was added 4-dimethylamino)pyridine (1.00 mmol) and phenyl chlorothioformate (0.60 mmol), and then the reaction mixture was allowed to warm to stir at room temperature for 5 hours. The mixture was partitioned between methylene chloride and brine, and the organic layer washed with brine, dried over anhydrous magnesium sulfate, and filtered. The volatiles were removed and the phenyl thioester containing residue was used in the following radical reaction without further purification.

To a stirred solution of the phenyl thioester containing residue in dry benzene was added triethylborane (1.00 mmol, 1.0 M solution in hexanes) and tributyltin hydride (1.00 mmol), and the reaction mixture stirred overnight at ambient temperature. The mixture was evaporated, and the residue was purified by silica gel column chromatography (methylene chloride:methanol=20:1) to give the deoxygenated product.

To a stirred solution of the deoxygenated product in tetrahydrofuran (5 ml) was added dropwise tetra-n-butylammonium fluoride (1.20 mmol, 1.0 M in tetrahydrofuran) and the mixture stirred at room temperature for 5 hours. After the removal of solvent, the residue was purified by flash silica gel column chromatography (methylene chloride:methanol=5:1) to afford a 2'-deoxygenated uracil derivative of Table 3, which was crystallized from diethyl ether/methanol.

TABLE 3

2'-Deoxygenated Uracil Derivatives

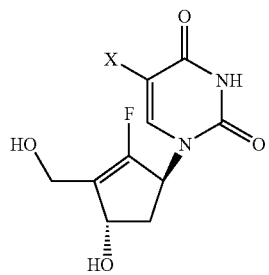

| No | Name | X | Formula | MW |
|----|------|---|---------|-----|
| 30 | RX-3216 | H | $C_{10}H_{11}FN_2O_4$ | 242.2 |
| 31 | RX-3216A | F | $C_{10}H_{10}F_2N_2O_4$ | 260.2 |
| 32 | RX-3216B | Cl | $C_{10}H_{10}ClFN_2O_4$ | 276.7 |
| 33 | RX-3216C | Br | $C_{10}H_{10}BrFN_2O_4$ | 321.1 |
| 34 | RX-3216D | I | $C_{10}H_{10}FIN_2O_4$ | 368.1 |
| 35 | RX-3216E | CH$_3$ | $C_{11}H_{13}FN_2O_4$ | 256.2 |

Yields and spectroscopic data for deoxygenated uracil derivatives 30-35 were as follows:

(1S,4R)-1-(2-Fluoro-4-hydroxy-3-hydroxymethyl-cyclopent-2-enyl)-1H-pyrimidine-2,4-dione (30, RX-3216). 63.0 mg, 52%; $^1$H NMR (400 MHz, CD$_3$OD) δ 7.50 (d, J=8.0 Hz, 1H), 5.85 (d, J=8.0 Hz, 1H), 5.52 (bs, 1H), 4.62 (d, J=12.8 Hz, 1H), 4.39 (d, J=12.8 Hz, 1H), 4.25 (m, 1H), 2.05-2.18 (m, 2H).

(1S,4R)-5-Fluoro-1-(2-fluoro-4-hydroxy-3-hydroxymethyl-cyclopent-2-enyl)-1H-pyrimidine-2,4-dione (31, RX-3216A). 63.7 mg, 49%; $^1$H NMR (400 MHz, CD$_3$OD) δ 7.75 (d, J=6.4 Hz, 1H), 5.55 (bs, 1H), 4.65 (d, J=12.8 Hz, 1H), 4.34 (d, J=12.8 Hz), 4.15 (m, 1H), 2.04-2.20 (m, 2H).

(1S,4R)-5-Chloro-1-(2-fluoro-4-hydroxy-3-hydroxymethyl-cyclopent-2-enyl)-1H-pyrimidine-2,4-dione (32, RX-3216B). 65.0 mg, 47%; $^1$H NMR (400 MHz, CD$_3$OD) δ 8.39 (s, 1H), 5.35 (bs, 1H), 4.69 (d, J=12.8 Hz, 1H), 4.37 (d, J=12.8 Hz, 1H), 4.20 (m, 1H), 2.05-2.18 m, 2H).

(1S,4R)-5-Bromo-1-(2-fluoro-4-hydroxy-3-hydroxymethyl-cyclopent-2-enyl)-1H-pyrimidine-2,4-dione (33, RX-3216C). 72.2 mg, 45%; $^1$H NMR (400 MHz, CD$_3$OD) δ 8.57 (s, 1H), 5.35 (bs, 1H), 4.69 (d, J=12.8 Hz, 1H), 4.37 (d, J=12.8 Hz, 1H), 4.20 (m, 1H), 2.08-2.22 (m, 2H).

(1S,4R)-1-(2-Fluoro-4-hydroxy-3-hydroxymethyl-cyclopent-2-enyl)-5-iodo-1H-pyrimidine-2,4-dione (34, RX-3216D). 75.5 mg, 41%; $^1$H NMR (400 MHz, CD$_3$OD) δ 8.69 (s 1H), 5.39 (bs, 1H), 4.67 (d, J=12.8 Hz, 1H), 4.37 (d, J=12.8 Hz, 1H), 4.16 (m, 1H), 2.01-2.17 (m, 2H).

(1S,4R)-1-(2-Fluoro-4-hydroxy-3-hydroxymethyl-cyclopent-2-enyl)-5-methyl-1H-pyrimidine-2,4-dione (35, RX-3216E). 67.9 mg, 53%; $^1$H NMR (400 MHz, CD$_3$OD) δ 7.72 (s. 1H), 5.39 (bs, 1H), 4.68 (d, J=12.8 Hz, 1H), 4.37 (d, J=12.8 Hz, 1H), 4.15 (m, 1H), 2.10-2.25 (m, 2H).

General Procedure for the Conversion to Cytosine Derivatives

A solution of a uracil compound of Table 3 (0.5 mmol) in anhydrous pyridine (5 ml) was treated with acetic anhydride (470 µl, 5.0 mmol), and the mixture stirred at ambient temperature for 5 hours. The residue obtained after evaporation of all the volatiles was diluted with methylene chloride; washed with diluted HCl, saturated NaHCO$_3$ solution and brine; dried (MgSO$_4$); filtered, and evaporated. The triacetate containing residue was used in the next step without further purification.

A solution of 1,2,4-triazole (760 mg, 11.0 mmol) and phosphorous oxychloride (915 µl, 10.0 mmol) in acetonitrile (10 ml) was treated with triethylamine (1.25 ml, 9.0 mmol) and triacetate (1.00 mmol) in 4 ml of acetonitrile. The reaction mixture was stirred at room temperature for 15 hours. Additional triethylamine (1.5 ml) and water (4.5 ml) were added, and the mixture was stirred for 10 minutes. After dilution with methylene chloride, the mixture was washed with saturated NaHCO$_3$ solution and brine, dried (MgSO$_4$), filtered, and evaporated. The residue was used in the next step without further purification.

To a solution of the above residue in 1,4-dioxane (8 ml) was added ammonium hydroxide (28%, 2 ml) at 0° C., and the reaction mixture was stirred at ambient temperature for 10 hours. After removal of all volatiles, the residue was dissolved in methanolic ammonia (5 ml) and stirred at ambient temperature for 12 hours. The reaction mixture was evaporated, and the residue was purified by ODS column chromatography (water:acetone=20:1) to give the 2'-deoxygenated cytosine derivative of Table 4, which was crystallized from diethyl ether/methanol.

TABLE 4

2'-Deoxygenated Cytosine Derivatives

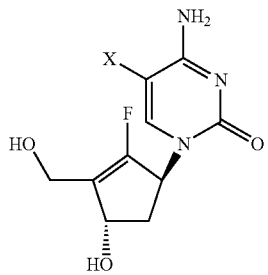

| No | Name | X | Formula | MW |
|---|---|---|---|---|
| 36 | RX-3217 | H | C$_{10}$H$_{12}$FN$_3$O$_3$ | 241.2 |
| 37 | RX-3217A | F | C$_{10}$H$_{11}$F$_2$N$_3$O$_3$ | 259.2 |
| 38 | RX-3217B | Cl | C$_{10}$H$_{11}$ClFN$_3$O$_3$ | 275.7 |
| 39 | RX-3217C | Br | C$_{10}$H$_{11}$BrFN$_3$O$_3$ | 320.1 |
| 40 | RX-3217D | I | C$_{10}$H$_{11}$FIN$_3$O$_3$ | 367.1 |

Yields and spectroscopic data for the deoxygenated cytosine derivatives 36-40 were as follows:

(1S,4R)-4-Amino-1-(2-fluoro-4-hydroxy-3-hydroxymethyl-cyclopent-2-enyl)-1H-pyrimidine-2-one (36, RX-3217). 63.9 mg, 53%; $^1$H NMR (400 MHz, CD$_3$OD) δ 7.48 (d, J=8.0 Hz, 1H), 5.95 (d, J=8.0 Hz, 1H), 5.40 (bs, 1H), 4.37 (d, J=12.8 Hz, 1H), 4.20 (m, 1H), 4.08 (d, J=12.8 Hz, 1H), 2.04-2.19 (m, 1H)

(1S,4R)-4-Amino-5-fluoro-1-(2-fluoro-4-hydroxy-3-hydroxymethyl-cyclopent-2-enyl)-1H-pyrimidin-2-one (37, RX-3217A). 53.1 mg, 41%; $^1$H NMR (400 MHz, CD$_3$OD) δ 7.81 (d, J=6.4 Hz, 1H), 5.39 (bs, 1H), 4.37 (d, J=12.8 Hz, 1H), 4.25 (m, 1H), 4.11 (d, J=12.8 Hz, 1H), 2.08-2.21 (m, 1H).

(1S,4R)-4-Amino-5-chloro-1-(2-fluoro-4-hydroxy-3-hydroxymethyl-cyclopent-2-enyl)-1H-pyrimidin-2-one (38, RX-3217B). 62.0 mg, 45%; $^1$H NMR (400 MHz, CD$_3$OD) δ 8.51 (s, 1H), 5.39 (bs, 1H), 4.45 (d, J=12.8 Hz, 1H), 4.23 (m, 1H), 4.18 (d, J=12.8 Hz, 1H), 2.05-2.16 (m, 2H).

(1S,4R)-4-Amino-5-bromo-1-(2-fluoro-4-hydroxy-3-hydroxymethyl-cyclopent-2-enyl)-1H-pyrimidin-2-one (39, RX-3217C). 76.8 mg, 48%; $^1$H NMR (400 MHz, CD$_3$OD) δ 8.61 (s, 1H), 5.46 (bs, 1H), 4.41 (d, J=12.8 Hz, 1H), 4.23 (m, 1H), 4.16 (d, J=12.8 Hz, 1H), 2.08-2.17 (m, 2H).

(1S,4R)-4-Amino-1-(2-fluoro-4-hydroxy-3-hydroxymethyl-cyclopent-2-enyl)-5-iodo-1H-pyrimidin-2-one (40, RX-3217D). 64.2 mg, 35%; $^1$H NMR (400 MHz, CD$_3$OD) δ 8.63 (s, 1H), 5.38 (s, 1H), 4.35 (d, J=12.8 Hz, 1H), 4.19 (m, 1H), 4.11 (d, J=12.8 Hz, 1H), 2.11-2.23 (m, 2H).

Example 3

Cell Growth Inhibition of Nucleoside Compounds

Growth of Cancer Cell Lines

Cancer cell lines to determine the effect of nucleoside compounds were obtained from the following sources: Human OVCAR-3 (ovary), MCF-7 (breast, hormone-dependent), MDA-MB-231 (breast), HeLa (cervix), PC3 (prostate), LNCap (prostate), HepG2 (liver), A549 (lung), NCI-H226 (lung), HT-29 (colon), HCT116 (colon), SK-MEL-28 (melanoma) and PANC-1 (pancreas) from the American Type Culture Collection (ATCC) (Manassas, Va.); U251 (brain) from Riken (Japan); MKN-45 (stomach) from DSMZ (Germany); UMRC2 (kidney) from the United States National Cancer Institute (Bethesda, Md.). All cell lines except MDA-MB-231, HCT116, UMRC2 and PANC-1 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 µg/ml streptomycin ("P/S"). MDA-MB-231, HCT116, UMRC2 and PANC-1 cells were maintained in Dulbecco's modified Eagle's medium ("DMEM", Invitrogen) supplemented with 10% FBS, P/S, 10 mM HEPES and 2 mM L-glutamine. All cells were incubated at 37° C. under humidified 5% CO$_2$.

Cell Growth Inhibition Assay

The growth inhibition of the nucleoside derivatives against a variety of human tumor cells can be evaluated. The relative importance of particular substituent groups on the compounds can be studied. The nucleoside derivatives, prepared as described above, are tested with DMSO as a control.

The growth inhibition assay of RX-3117 against 16 human tumor cell lines was performed using the Sulforhodamine B ("SRB") method (Skehan et al., J. National Cancer Institute, 82: 1107-1112 (1990)). Briefly, exponentially growing tumor cells were seeded into a 96-well plate at a density of 2-3×10$^3$ cells/well and treated with nucleoside compounds the next day. Triplicate wells were used for each treatment. The cells were incubated with the various compounds for 96 hours at 37° C. in a humidified 5% CO$_2$ atmosphere. After 96-hour incubation, cells were fixed with 10% trichloroacetic acid ("TCA"), incubated for 1 hour at 4° C., and washed 3 times with tap water. Subsequently, cells were stained with 0.4% sulforhodamine B in 1% acetic acid for 30 minutes, washed 4 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.).

To translate the $OD_{530}$ values into the number of live cells in each well, the $OD_{530}$ values were compared to those on standard $OD_{530}$—versus—cell number curves generated for each cell line. The percent survival was calculated using the formula:

% Survival=live cell number[test]/live cell number [control]×100

The $IC_{50}$ values were calculated by non-linear regression analysis.

Table 5 summarizes the inhibition of cell growth ($IC_{50}$, µM) determined for RX-3117.

TABLE 5

Inhibition of cell growth ($IC_{50}$, µM) by RX-3117 against human cancer cell lines

| MDA-MB-231 | HCT116 | NCI-H226 | HT-29 | MKN-45 | MCF-7 | A549 | PANC-1 |
|---|---|---|---|---|---|---|---|
| 0.18 | 0.19 | 0.25 | 0.28 | 0.34 | 0.34 | 0.50 | 0.62 |

| PC3 | HepG2 | OVCAR-3 | U251 | UMRC2 | HeLa | SK-MEL-28 | LnCap |
|---|---|---|---|---|---|---|---|
| 0.63 | 0.79 | 0.80 | 0.83 | 0.83 | 1.35 | 1.38 | 2.67 |

As shown in Table 5, nucleoside derivatives of the invention are active against a broad range of tumor cell lines.

Example 4

Ex Vivo Xenograft Study

In order to observe the inhibition of growth of tumor in an animal model, an ex vivo xenograft study of nude mice was conducted utilizing RX-3117. Suitable human cancer cell lines are those that have been tested already for inhibition of cancer cell growth, and particularly preferred was colon carcinoma HCT116. The antitumor efficacy of RX-3117 was evaluated against subcutaneously injected tumor xenografts in nude mice and tumor volume was measured after the treatment of RX-3117.

HCT116 cell suspension ($2\times10^6$ cells in 0.1 ml of RPMI) was injected subcutaneously into the right flank of six-week-old male athymic mice (BALB/c nu/nu) on day 0. A sufficient number of mice were injected with HCT116 cell suspension so that tumors in a volume range as narrow as possible were selected for the trial on the day of treatment initiation. Animals with tumors in the proper size range were assigned to various treatment groups. RX-3117 was dissolved in 10% DMSO in PBS and solvent alone served as control. All study medications (control, RX-3117: 2 mg/kg/day, RX-3117: 10 mg/kg/day) were given by intraperitoneal injections three times per week starting from day 5 and ending on day 37. To quantify tumor growth, three perpendicular diameters of the tumors were measured with calipers every 3-5 days, and the body weight of the mice was monitored for toxicity. The tumor volume was calculated using the formula: tumor volume ($mm^3$)=(width)×(length)×(height)×π/6.

Tumor volume (mean±SEM) in each group of animals is presented in FIG. 1, which shows a measurement of tumor volume as an indicator of efficacy of RX-3117 against HCT116 human colon carcinoma xenografts. The RX-3117 treatment was well tolerated without deaths and no more than 1 g body weight fluctuations was observed. After day 37, the tumor volume was significantly reduced in the mice treated with RX-3117 at 2 and 10 mg/kg treatment compared to the controls. Thus, as demonstrated in FIG. 1, RX-3117 causes the inhibition of tumor growth in nude mice sc-injected with HCT116 human colon carcinoma cells.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A compound of the formula:

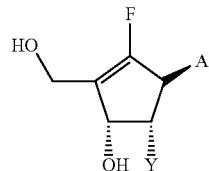

wherein:

A is selected from

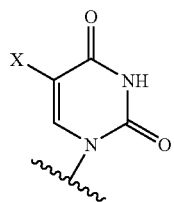 and 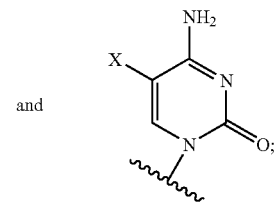

Y=H or OH and X=H, F, Cl, Br, I, or $CH_3$;

or a pharmaceutically acceptable salt thereof with the proviso that, when A is

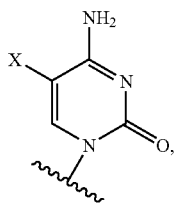

X is not CH₃.

2. The compound of claim 1 having the formula

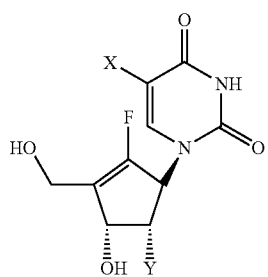

wherein: Y=H or OH and X=H, F, Cl, Br, I, or CH₃ or a pharmaceutically acceptable salt thereof.

3. A compound of claim 1, having the formula:

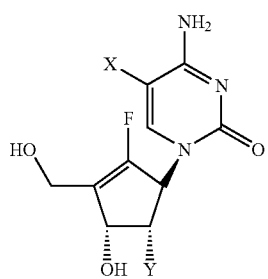

wherein: Y=H or OH and X=H, F, Cl, Br or I or a pharmaceutically acceptable salt thereof.

4. The compound of claim 1 that is:

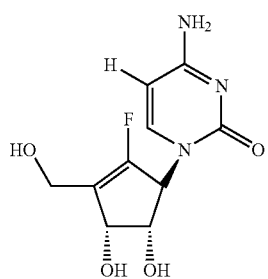

or a pharmaceutically acceptable salt thereof.

5. The compound according to claim 1 having an IC$_{50}$ of not greater than 10 μM with respect to at least one cell line for a tumor selected from tumors of the ovary, tumors of the breast, cervical tumors, tumors of the prostate, tumors of the liver, lung tumors, kidney tumors, colon tumors, pancreatic tumors, brain tumors, stomach tumors and melanoma.

6. The compound according to claim 5, wherein said cell line is selected from Human OVCAR-3 for tumors of the ovary, MCF-7 or MDA-MB-231 for breast tumors, HeLa for cervical tumors, PC3 or LNCap for tumors of the prostate, HepG2 for tumors of the liver, A549 or NCI-H226 for lung tumors, UMRC2 for kidney tumors, HT-29 or HCT116 colon tumors, PANC-1 for pancreatic tumors, U251 for brain tumors, MKN-45 for stomach tumors and SK-MEL-28 for melanoma.

7. The compound of claim 5, having an IC$_{50}$ of not greater than 1.0 μM.

8. The compound of claim 5, having an IC$_{50}$ of not greater than 0.5 μM.

9. A pharmaceutical composition comprising a therapeutically effective amount of a compound according to claim 1, or a pharmaceutically acceptable salt thereof, and a pharmaceutically acceptable carrier or diluent.

10. A method of synthesizing a compound of formula:

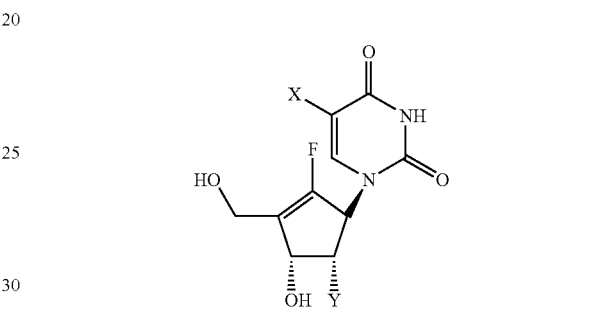

wherein: Y=H or OH and X=H, F, Cl, Br, I, or CH₃ or a compound of the formula

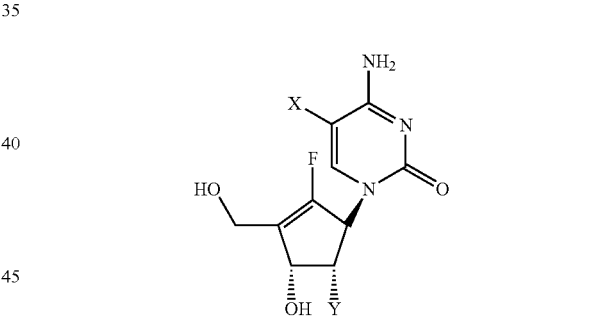

wherein: Y=H or OH and X=H, F, Cl, Br, or I, comprising at least one step selected from the group:

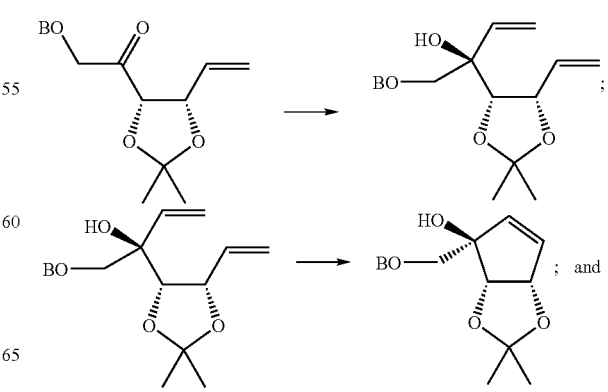

-continued

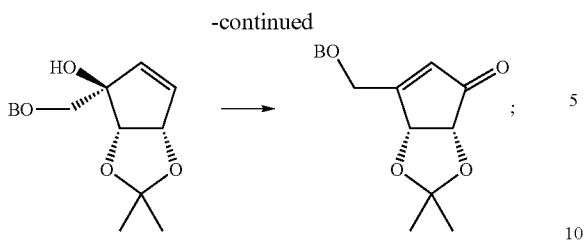

wherein B is selected from tert-butyldimethyl silyl, tert-butyldiphenyl silyl, and trityl.

11. The method of claim 10, wherein B is trityl.

12. A method for treating a tumor comprising administering a composition comprising a compound of the formula:

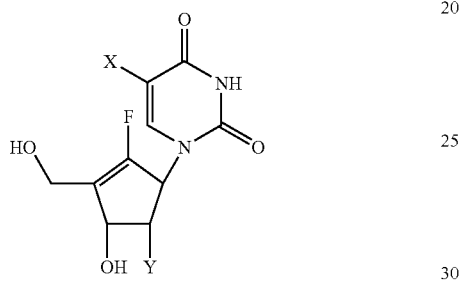

wherein: Y=H or OH and X=H, F, Cl, Br, I, or CH$_3$ or a compound of the formula

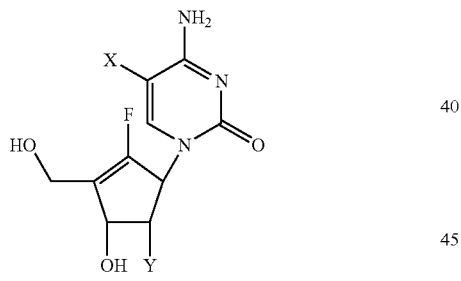

wherein: Y=H or OH and X=H, F, Cl, Br, or I, or a pharmaceutically acceptable salt thereof to a subject in need of such treatment, and thereby treating the tumor.

13. The method of claim 12, wherein the compound is

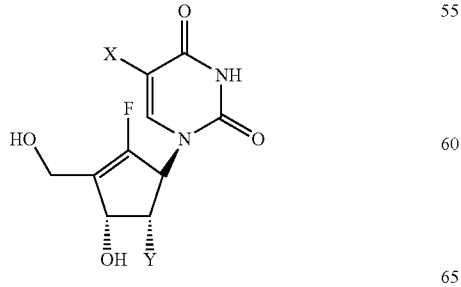

wherein: Y=H or OH and X=H, F, Cl, Br, I, or CH$_3$

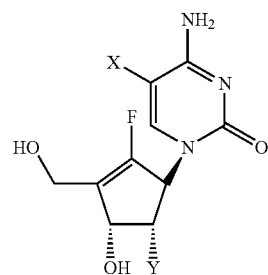

wherein: Y=H or OH and X=H, F, Cl, Br, or I, or a pharmaceutically acceptable salt thereof.

14. The method of claim 12, wherein the compound or salt has the formula:

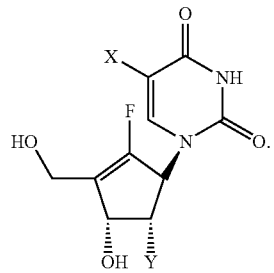

15. The method of claim 12, wherein the compound or salt has the formula:

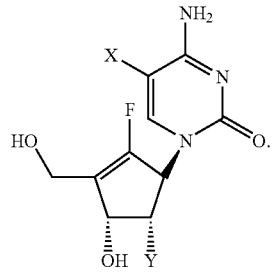

16. The method of claim 12, wherein the compound is:

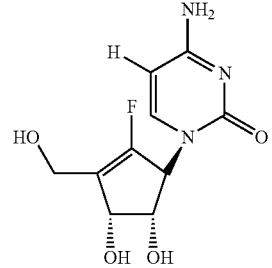

or a pharmaceutically acceptable salt thereof.

17. The method of claim 12, said composition further comprising a pharmaceutically acceptable carrier or diluent.

18. The method of claim 12, said tumor selected from tumors of the ovary, tumors of the breast, cervical tumors, tumors of the prostate, tumors of the liver, lung tumors, kidney tumors, colon tumors, pancreatic tumors, brain tumors, stomach tumors and melanoma.

* * * * *